US00PP32697P2

(12) United States Plant Patent
Horvath

(10) Patent No.: US PP32,697 P2
(45) Date of Patent: Dec. 22, 2020

(54) ***SEDUM* PLANT NAMED 'SUNSET BOULEVARD'**

(50) Latin Name: ***Sedum* hybrid**
Varietal Denomination: Sunset Boulevard

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 16/602,960

(22) Filed: Jan. 3, 2020

(51) Int. Cl.
*A01H 5/02* (2018.01)
*A01H 6/32* (2018.01)

(52) U.S. Cl.
USPC ..... Plt./479

(58) Field of Classification Search
USPC ..... Plt./479
CPC ... A01H 5/02; A01H 5/00; A01H 5/12; A01H 6/32; A01H 6/328
See application file for complete search history.

(56) References Cited

PUBLICATIONS

Issuu Delaware Center for Horticulture's 39th Annual Rare Plant Auction 2019, retrieved on Jun. 25, 2020, retrieved from the Internet at https://issuu.com/thedch/docs/2019_rpa_catalog_final_high_res, cover p. 19, 53. (Year: 2019).*

* cited by examiner

*Primary Examiner* — June Hwu

(57) ABSTRACT

A new, distinct *Sedum* plant as illustrated and described, characterized by large gray-green foliage, RHS 70 A color flowers, and taller height.

1 Drawing Sheet

Latin name: *Sedum* hybrid.
Cultivar name: 'Sunset Boulevard'.

BACKGROUND OF THE INVENTION

The present invention relates to a new and distinct hybrid of *Sedum* plant named 'Sunset Boulevard' characterized by larger gray-green foliage, red-purple color flowers, taller height compared to the seed parent. The new *Sedum* was raised as a seedling from open pollinated seed sown as an unnamed *Sedum ussuriense*, not patented, in Hebron, Ill. in 2013. The selection of the new plant was due to its' larger gray-green foliage, deep red-purple color flowers, taller height, compared to the seed parent. Initial asexual reproduction has taken place at a nursery in Hebron, Ill. since 2015 by means of division, and vegetative stem cuttings. The new *Sedum* has shown to be stable and identical in reproduction to the originally discovered plant after rooting over 1400 plants from 2015 to 2018. No plants of the new *Sedum* have been sold in this country, or anywhere in the world, prior to the filing of this application, nor has any disclosure of the new plant been made prior to the filing of this application with the exception of that which was disclosed by the inventor and his company, Intrinsic Perennial Gardens, Inc within one year of filing of this application and was derived directly from the inventor.

SUMMARY OF THE INVENTION

The new *Sedum* plant named 'Sunset Boulevard' characterized by larger gray-green foliage, red-purple color flowers, taller height, compared to the seed parent have been observed to be unique and stable.

Plants of the new *Sedum* can be compared to plants of *Sedum spectabile* 'Brilliant' not patented. 1. The new *Sedum* plant has a mature size measuring 50 cm high and up to 70 cm wide while *Sedum spectabile* measures 45-55 cm high and 55-65 cm wide. 2. The new *Sedum* has red-purple flowers colored RHS 70 A, while *Sedum spectabile* is entirely pink.

Plants of the new *Sedum* can also be compared to the seed parent plant, an unnamed, *Sedum ussuriense*, not patented. 1. The new *Sedum* has a mature size of 50 cm high and 70 cm wide while the seed parent has a mature size of 30 cm high and 30 cm wide. 2. The new *Sedum* has larger foliage measuring on average up to 7 cm long by 4 cm wide while the seed parent has foliage measuring 40 mm long by 35 mm wide. 3. The new *Sedum* has a stem diameter of 7 mm while the seed parent has stem diameter of 3 mm. 4. The new *Sedum* has red-purple flowers colored RHS 70 A, compared to the mostly red flowers of the seed parent.

DESCRIPTION OF PHOTOGRAPHS

Figure 1:
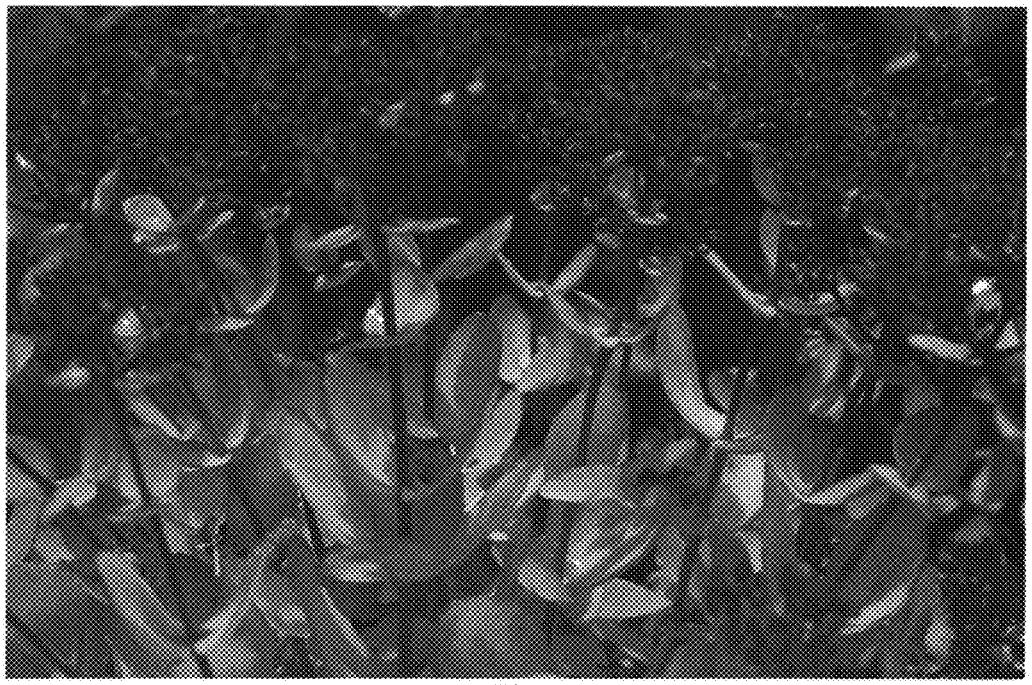
Figure 2:
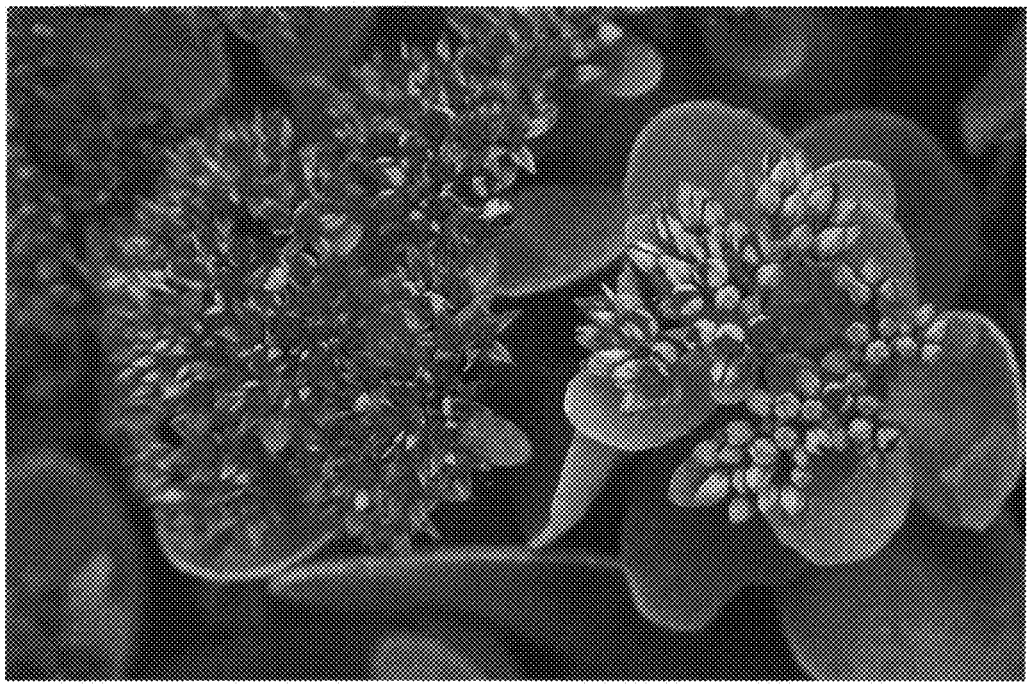

Plants pictured in the drawing were grown for two years.
FIG. 1. Close up of the foliage in fall color.
FIG. 2. Close up of the flower.

DETAILED BOTANICAL DESCRIPTION

In the following description, color references are made to The Royal Horticultural Society Colour Chart (2001). Plants used for the description were grown for two years at a nursery in Hebron, Ill., USA. Measurements and numerical values represent averages of typical plants.

Botanical classification: *Sedum* hybrid cultivar Sunset Boulevard.

Parentage: Male or pollen unknown and female or seed an open pollinated, unnamed *Sedum ussuriense*.

Propagation: Vegetative division and stem cutting propagation.

Plant description: Overall habit of the new *Sedum* is basal clumps, with upright stems topped by red-purple color flowers in September. Growth rate of the new *Sedum* plant is vigorous.

*Plant height*.—Average 50 cm.
*Plant width*.—Up to 70 cm.
*Stem color*.—Close to 174 A, 187 B and C below the flower.
*Stem shape*.—Both typical and observed — round.
*Stem texture*.—Glabrous.
*Stem length*.—44 cm.
*Stem diameter*.—7 mm.
*Internode length*.—3 cm.

Foliage:

*Type*.—Deciduous.
*Shape*.—Obovate.
*Petiole*.—None.
*Length*.—7 cm.
*Width*.—4 cm.
*Thickness*.—2-3 mm.
*Margin*.—Dentate.
*Leaf apex, typical and observed*.—Obtuse.
*Leaf bases, typical and observed*.—Cuneate.
*Upper and lower leaf texture*.—Smooth.
*Leaf arrangement*.—Alternate, crowded except at the base of the stems.
*Leaf venation pattern*.—Arcuate.
*Leaf vein color*.—Primary vein color 145 B on the top and 145A on the bottom.
*Adaxial leaf description*.—Color is 145 B.
*Abaxial leaf description*.—Color is 145 A.
*Fall foliage color*.—Adaxial 184 C toward the tip of the leaf, 152 C toward the base. Abaxial 186 B toward the tip of the leaf, 145 C toward the base.

Flower:

*Petal count*.—5.
*Petal shape*.—Lanceolate.
*Adaxial petal color*.—70 A.
*Abaxial petal color*.—70 B.
*Petal apex shape*.—Acuminate.
*Petal base*.—1-2 mm wide.
*Petal length*.—8 mm.
*Petal width*.—2 mm.
*Petal margin, typical and observed*.—Entire.
*Petal bases, typical and observed*.—Obtuse.
*Inflorescence type*.—Panicle on basal flowering stems.
*Panicle color*.—As a whole the color is close to 71 A.
*Inflorescence size*.—14 cm across, 9 cm tall.
*Inflorescence length*.—14 cm.
*Inflorescence width*.—14 cm.
*Flower number*.—Approximately 400 per panicle.
*Individual flower size*.—9-10 mm across, 12 mm tall.
*Bloom period and duration*.—Late August to the end of September, lasting three to four weeks.
*Bud shape, typical and observed*.—Elliptical.
*Bud length, typical and observed*.—7 mm.
*Bud diameter, typical and observed*.—3 mm.
*Bud color, typical and observed*.—Overall 186 C with some parts N80 B.
*Sepal size*.—1 mm across, 2 mm tall.
*Sepal number*.—5.
*Sepal shape, typical and observed*.—Narrow ovate.
*Sepal apex, typical and observed*.—Acute.
*Sepal margin, typical and observed*.—Entire.
*Sepal color, abaxial and adaxial typical and observed*.—Close to 186 C.
*Peduncle length, typical and observed*.—4-5 cm.
*Peduncle diameter, typical and observed*.—2-3 mm.
*Peduncle color, typical and observed at the beginning of the season usually April, May, and June*.—Close to 139 A. As the season progresses usually July, August, September, and October typical and observed peduncle color can be — 177 A.
*Pedicel length, typical and observed*.—3 mm.
*Pedicel diameter, typical and observed*.—1 mm.
*Pedicel color, typical and observed at the beginning of the season usually April, May, and June*.—Close to 139 A. As the season progresses usually July, August, September, and October typical and observed peduncle color can be — 177 A.
*Carpel color*.—71 A.
*Carpel surfaces*.—Glabrous.
*Carpel number*.—5 per flower.
*Carpel length*.—2 mm, Carpel width — 1 mm.
*Stigma shape*.—Capitate, Stigma size.—4 mm, Stigma color.—71 A.
*Style length*.—2 mm, Style shape slender, Style color.—71 A.
*Ovary size*.—3 mm long and 1-2 mm wide.
*Ovary shape*.—Cordate, Ovary color.—71 A.
*Fertility*.—Sterile, 10 anthers, 10 stamens at 7 mm long, color 71 A.
*Anther color*.—Close to 187 A, Pollen color — too sparce to observe.
*Blooming habit*.—Domed, terminal panicle on up to 60 cm stems.
*Scent*.—No scent noticed.
*Fruit*.—None noticed.
*Hardiness*.—U.S.D.A. hardiness zones 4-9.
*Disease resistance*.—Resistance to diseases common to *Sedum* has not been observed on plants grown under nursery conditions.
*Pest resistance*.—Resistance to pests common to *Sedum* has not been observed on plants grown under nursery conditions.

I claim:

1. A new, distinct *Sedum* plant as illustrated and described, characterized by larger gray-green foliage, RHS 70 A color flowers, and taller height, compared to the seed parent.

* * * * *